United States Patent [19]

Huber et al.

[11] Patent Number: 5,032,518

[45] Date of Patent: Jul. 16, 1991

[54] HAPTEN-PROTEIN CONJUGATES AND THE USE THEROF

[75] Inventors: Erasmus Huber, Garching; Hans-Georg Batz, Tutzing; Herbert von der Eltz; Christian Klein, both of Weilheim, all of Fed. Rep. of Germany

[73] Assignee: Boehringer Mannheim GmbH, Mannheim, Fed. Rep. of Germany

[21] Appl. No.: 301,644

[22] Filed: Jan. 25, 1989

[30] Foreign Application Priority Data

Jan. 25, 1988 [DE] Fed. Rep. of Germany ....... 3802060

[51] Int. Cl.$^5$ ..................... C07K 17/12; C12N 11/12; C12Q 1/28

[52] U.S. Cl. .................................. 435/178; 435/174; 435/188; 435/192; 435/207; 530/363; 530/387; 530/405; 530/406; 530/395

[58] Field of Search ............... 530/395, 405, 406, 363, 530/387; 435/178, 188, 174, 207, 192

[56] References Cited

U.S. PATENT DOCUMENTS

| | | | |
|---|---|---|---|
| 4,194,048 | 3/1980 | Buckler | 548/312 |
| 4,218,539 | 8/1980 | Weltman | 435/188 |
| 4,277,460 | 7/1981 | Kojima et al. | 424/1.1 |
| 4,378,428 | 3/1983 | Fatina et al. | 435/7 |
| 4,550,019 | 10/1985 | Polson | 424/85.91 |
| 4,740,476 | 8/1988 | Kubodera et al. | 436/518 |

FOREIGN PATENT DOCUMENTS 0218347 4/1987 European Pat. Off. .
2165046 4/1986 United Kingdom .

OTHER PUBLICATIONS

Blair et al. (1983) J. Immunol. Methods 59:129–143.
Erlanger et al. (1959) J. Biol. Chem. 234:1090–1094.
Monsigny et al. (1980) FEBS Lett. 119(1):181–185.

*Primary Examiner*—Jeffrey E. Russel
*Assistant Examiner*—Kay Kim
*Attorney, Agent, or Firm*—Felfe & Lynch

[57] ABSTRACT

The present invention provides a hapten-protein conjugate, wherein a hapten is bound to the reducing end of a sugar which consists of up to 10 monosaccharide units and on a free $CH_2OH$ group on the other end of the sugar, which is in the α-position to a hydroxyl group, is bound a protein.

12 Claims, No Drawings

HAPTEN-PROTEIN CONJUGATES AND THE USE THEROF

The present invention is concerned with hapten-protein conjugates and with the use thereof.

In clinical diagnosis, determination processes using immunoassays are being carried out more and more, these assays being characterized by extreme sensitivity. For this purpose, the substance to be determined is reacted with a specific, immunologically-active substance, which can be an antigen, a hapten or an antibody and which is provided with a label, and usually with at least one further specifically binding substance which is bound to a solid phase. After separation of the conjugate bound to the solid phase from the liquid phase which conjugate comprises a specifically-binding substance, a substance to be determined and a labelled, specifically-binding substance, in one of the two phases there can then be determined the amount of label, which is a measure of the substance to be determined. Enzymes are very frequently used as label.

There are very many variants for these immunoassays. For many purposes, competitive assays are, for example, carried out. The substance to be determined and a known amount of substance to be determined which is labelled with an enzyme compete for an antibody.

Therefore, on the one hand, there is a need for conjugates of a labelling enzyme and of a compound specifically bindable with the substance to be determined or an antibody, in which case the conjugate must only react with the substance to be determined or the antibody and must not show any cross-reactivity with other compounds present in the sample solution in order not to falsify the result. Since the specifically binding substance and the labelling enzyme are frequently not bound directly with one another but rather are coupled via a spacer, the affinity of the antibody to the spacer gives rise to problems.

Furthermore, there is a great need for specific antibodies. In general, antibodies are produced by injecting an immunogen, such as an antigen or hapten, in appropriate form several times into an organism capable of antibody formation. According to definition, haptens are molecules with a molecular weight of less than 1000 Dalton which alone are not immunogenically active but become immunogenic when bound to a protein. When used in immunization, the hapten is conjugated with an immunogenic molecule, for example a serum protein. If such a conjugate is injected, then, besides antiprotein antibodies, the organism forms the desired anti-hapten antibodies, the antibodies formed then being obtained from the organism. In this way, polyclonal antibodies can be obtained.

For the production of monoclonal antibodies, there must first be carried out an immunization of appropriate organisms which, as a rule, are mice. Due to the usually repeated injection of an antigen or hapten conjugate, a B cell is induced to synthesize and secrete antibodies against this antigen or hapten. By means of screening, a B cell which produces the desired antibodies is then isolated from the spleen and immortalized by fusion with a myeloma cell. This cell then continuously produces the same monoclonal antibodies.

In the case of the conjugates usually employed for the immunization, in which the hapten is bound to the immunogenic protein via a bridge, cross-reactions with the bridge molecule frequently occur and the antibodies obtained show, in part, a very high affinity for the bridge structure present in the immunogen. In immunological tests, this bridge recognition often gives rise to problems.

Therefore, it is an object of the present invention to provide hapten-protein conjugates which lead to the formation of antibodies specifically directed against the hapten and which have no affinity for the bridge molecule.

A further object of the present invention is to provide a hapten-protein conjugate which can be used in immunoassays and leads to a specific binding of antibodies to the hapten without cross-reactivity with the bridge molecule occurring.

Thus, according to the present invention, there is provided a hapten-protein conjugate, wherein a hapten is bound to the reducing end of a sugar which consists of up to 10 monosaccharide units and on a free $CH_2OH$ group on the other end of the sugar, either directly or via a bridge molecule or drops linking agent bound to said free $CH_2OG$ group which activates said sugar which free $CH_2OH$ group is in the a-position to a hydroxyl group, is bound a protein.

Surprisingly, by the use of a hapten-protein conjugate in which the hapten is bound to the protein via a sugar, it is possible to obtain antibodies which display very little cross-reactivity with the bridge compound, the antibodies obtained having a very high affinity for the hapten. Use of hapten-protein conjugate according to the present invention for in immunization protocols yields high antibody titres. Furthermore, the hapten-protein conjugates according to the present invention are especially suitable for use in immunoassays. Since the antibodies show no affinity to the bridge molecule and, therefore, very specifically only bind the hapten, more precise results are obtained when these congugates are used in immunoassays.

According to the present invention, the hapten is bound with the protein via a sugar. The sugar used as bridge can contain up to 10 monosaccharide units. Preferably, sugars are used with up to 5 monosaccharide units. The only thing that is important is that the sugar has a reducing end and, on the other end, has a free $CH_2OH$ group with a hydroxyl functional group in the a-position thereto. The monosaccharide units used have at least 5 carbon atoms, pyranoses and furanoses being especially used.

As sugars, there are preferably used compounds which are easily obtainable, such as glucose, maltose or maltopentaose, but lactose and cellobiose, as well as saccharide units having the branched structure of amylopectin can also be used.

The sugar is bound to the hapten either directly or through a bridge molecule or crosslinker via its reducing end. Binding takes place in known manner via functional groups of the hapten. If the hapten contains a hydroxyl group, then the binding between the lactol group of the sugar and the hydroxyl group takes place by acetal formation. If the hapten does not possess an appropriate functional group, then an appropriate group must be introduced. The binding of the hapten to the sugar must, in any case, take place in such a manner that its epitope remains freely accessible.

Before the reaction with the hapten, the sugar is usually peracetylated. After the reaction with the hapten, the protective groups are split off in known manner and the free $CH_2OH$ group is then selectively derivatized or activated by, e.g., binding an activating bridge molecule or crosslinker thereto.

For binding the glucose-hapten conjugate to an appropriate protein, the free $CH_2OH$ group of the sugar is activated, this taking place in known manner. For the activation of the sugar, there can be used known compounds, appropriate ones including, for example, N-hydroxysuccinimide esters.

The activated glucose-hapten conjugate is then coupled under standard conditions with a free $\epsilon$-amino group of the desired protein. As proteins, there can be used the immunogenic carrier proteins usually employed, for example edestin or bovine serum albumin. As enzymes, it is preferred to use $\beta$-galactosidase or peroxidase.

In an especially preferred embodiment of the present invention, hapten-protein conjugates are provided which consist of a steroid hormone, a sugar bridge and an immunogenic protein. The detection of steroid hormones, for example estrogen, testosterone, cortisone and the heart glucosides, the basic steroid structure of which is common to all of them, is very important for diagnosis. Therefore, it is very desirable to have available antibodies against steroid hormones, as well as steroid hormone-enzyme conjugates, in order to perform immunoassays. It has now proved to be very advantageous to derivatize steroid hormones so that they carry a hydroxyl group at the $C_6$ atom. This hydroxyl group can then react with the lactol group of the sugar bridge in known manner with acetal formation. This binding does not impair the epitope of the steroid hormone and does not result in any undesired changes of the molecule. Depending upon the purpose of use, either an immunization protein or an enzyme can be coupled on to the conjugate of steroid hormone and sugar bridge.

The hapten-protein conjugates according to the present invention can be used for immunization. When employed for immunization, a conjugate is preferably used in which the protein is an immunogenic carrier protein, for example edestin or bovine serum albumin. However, conjugates which contain enzymes as protein can also be used for immunization. A conjugate according to the present invention is injected several times at intervals into the organism appropriate for the antibody formation. The conjugate then brings about the formation of antibodies a very high percentage of which are only directed against the hapten but display no cross-reactivity with the sugar bridge. The antibodies can then be obtained from the organism in known manner. The hapten-carrier conjugates used according to the present invention are appropriate not only for immunization for the production of polyclonal antibodies but also for the production of monoclonal antibodies.

In a further embodiment of the present invention, a hapten-protein conjugate of a hapten which is bound via a sugar bridge to an enzyme is used for carrying out immunoassays. The so formed hapten-enzyme conjugate, can then be used as a label in determination processes according to the immunoassay principle. The conjugate formed from a hapten and a sugar bridge is thereby then reacted via the activated $CH_2OH$ group with a free $NH_2$ group of the enzyme.

The hapten-enzyme conjugate according to the present invention can then be added, for example, in known amount to a sample solution and then competes for an antibody directed against the hapten.

For immunization and for carrying out immunoassays, it has proved to be especially advantageous to use different conjugates which differ in the nature of the bridge. If, for the immunization, there is used one of the previously known bridge compounds, for example carboxymethoxime, dimethylcarboxymethoxime or hemisuccinate, then the hapten-enzyme conjugate used in the immunoassay should have a sugar bridge. If, for the immunoassay, antibodies are used which have been obtained by immunization with a hapten-protein conjugate according to the present invention then it has proved to be advantageous to use a hapten-enzyme conjugate with a known and preferably hydrophobic bridge.

The following Examples are given for the purpose of illustrating the present invention:

EXAMPLE 1

Procedure for the production of estradiol-6α-maltose-β-Gal immunogen

1. Oestradiol 3,17-diacetate (II)

600 ml. Acetic anhydride were mixed with 1.2 ml. perchloric acid, with stirring and cooling. Subsequently, 54.4 g. (200 mMole) estradiol (I) were added portionwise thereto at a temperature of 30° to 40° C. and the reaction mixture was stirred for 30 minutes at 25° C. The acetic anhydride was evaporated off in a high vacuum at a waterbath temperature of 40° C. and the residue was dissolved in 1 litre diethyl ether. The reaction mixture was then filtered through a fluted filter and the filtrate washed twice with, in each case, 500 ml. of saturated aqueous sodium hydrogen carbonate solution. The ethereal phase was separated off, washed with 500 ml. of water and dried with 50 g. anhydrous sodium sulphate. The solvent was evaporated off and the residue digested with 500 ml. petroleum ether. The solid product was filtered off with suction and dried in a desiccator over anhydrous calcium chloride.

2. 6-Oxoestradiol 3,17-diacetate (III)

35.6 g. (100 mMole) of (II) were dissolved in 500 ml. glacial acetic acid. 142 g. chromium trioxide dissolved in 820 ml. glacial acetic acid and 110 ml. water were added dropwise thereto at 20° C. and the reaction mixture was then stirred for 2 hours at 25° C. It was subsequently poured into 12 litres of water and extracted five times with 500 ml. amounts of dichloromethane. The combined organic extracts were washed with 1 litre of water, dried over 50 g. anhydrous sodium sulphate and evaporated.

The product (III) was separated from the viscous residue obtained (38 g.) by preparative column chromatography on silica gel (eluent: ethyl acetate/ petroleum ether 1:1 v/v). Yield: 12.5 g. (34% of theory) of a viscous oil.

3. 6 α-Hydroxyestradiol 3,17-diacetate (IV)

9.3 g. (25 mMole) of (III) were dissolved in 300 ml. anhydrous ethanol and 150 ml. anhydrous tetrahydrofuran, cooled to 0° C. and mixed, while stirring, with 3.8 g. (100 mMole) sodium borohydride. After 1.5 hours at 0° C., the reaction mixture was diluted with 1 litre diethyl ether, washed twice with, in each case, 500 ml. of water and dried over 30 g. anhydrous sodium sulphate. The solvent was evaporated off and the residue separated by preparative column chromatography on silica gel (eluent: ethyl acetate/petroleum ether 1:1 v/v). The product (IV) was obtained as a viscous, slowly crystallizing oil. Yield 4.2 g. (45% of theory).

4. Estradiol-6ε-maltoside peracetate (V)

3.7 g. (10 mMole) of (IV) were dissolved, together with 11.7 g. (15 mMole) heptaacetylmaltose trichloroacetimidate (preparation analogous to R.R. Schmidt and J. Michel, Angew. Chem., 92, 763/ 1980), in 100 ml. anhydrous dichloromethane. 1.5 ml. Boron trifluoride etherate in 5 ml. dichloromethane was added dropwise thereto, while stirring. After stirring for 1.5 hours, a further 0.1 ml. of boron trifluoride etherate in 5 ml. dichloromethane was added thereto and stirring continued for a further 15 minutes. The reaction mixture was then washed three times with, in each case, 50 ml. saturated aqueous sodium hydrogen carbonate solution and subsequently with 100 ml. of water. The organic phase was dried with 10 g. anhydrous sodium sulphate and evaporated. The product (V) was separated from the residue by preparative column chromatography on silica gel (eluent: ethyl acetate/ petroleum ether 3:2 v/v). Yield: 1.3 g. (31% of theory) of a viscous oil.

5. Estradiol-6α-maltoside (VI)

0.99 g. (1 mMole) of (V) were dissolved in 15 ml. methanol and mixed with 5 ml. 2N aqueous sodium hydroxide solution. The reaction mixture was stirred for 20 hours at 25° C., the pH was then adjusted to 5.0 by the addition of 2N hydrochloric acid and the solution was evaporated to dryness in a vacuum. The residue was dissolved in 10 ml. dimethylformamide, filtered and the filtrate evaporated to dryness in a high vacuum. The residue was digested with 10 ml. acetone, filtered off with suction and dried. The crude product was purified by preparative column chromatography on silica gel (eluent: chloroform/ methanol 3:2 v/v). Yield: 360 mg. (52% of theory).

6. Estradiol-6ε-maltose hemiglutaryl-N-hydroxy-succinimide ester (VII)

310 mg. (0.5 mMole) of (VI) were dissolved in 10 ml. anhydrous dimethylformamide and mixed with 1.75 g. (6 mMole) glutaric acid ω-0-trimethyl ester ω'-N-hydroxysuccinimide ester. After the addition of 300 mg. Nafion 117 and 2 g. of molecular sieve 4A, the reaction mixture was stirred for 20 hours in an inert gas atmosphere. Thereafter, it was filtered through a fluted filter, the filtrate was mixed with 2 ml. 0.1N hydrochloric acid and the solution was stirred for 15 minutes. The pH value was then adjusted to 5.0 with 0.1N aqueous sodium hydroxide solution and the solution evaporated to dryness in a high vacuum. The residue was again dissolved in 10 ml. anhydrous dimethylformamide, filtered and again evaporated to dryness. The residue was digested with 10 ml. anhydrous ethyl acetate, 10 ml. petroleum ether were then added thereto and the solid material was filtered off with suction. The product (VII) was washed with diethyl ether and dried in a high vacuum at 30° C. Yield 280 mg. (68% of theory).

7. Estradiol-maltose immunogen (VIII)

100 mg. of activated hapten (VIII) were dissolved in 5 ml. dimethylformamide and added to a solution of 1g. β-galactosidase in 0.5 litres of 0.1N phosphate buffer (pH 8.5). The reaction mixture was stirred for hours at 25° C., dialysed against water and lyophilized. The lyophilizate was used for the immunization.

The reaction scheme is illustrated in the following:

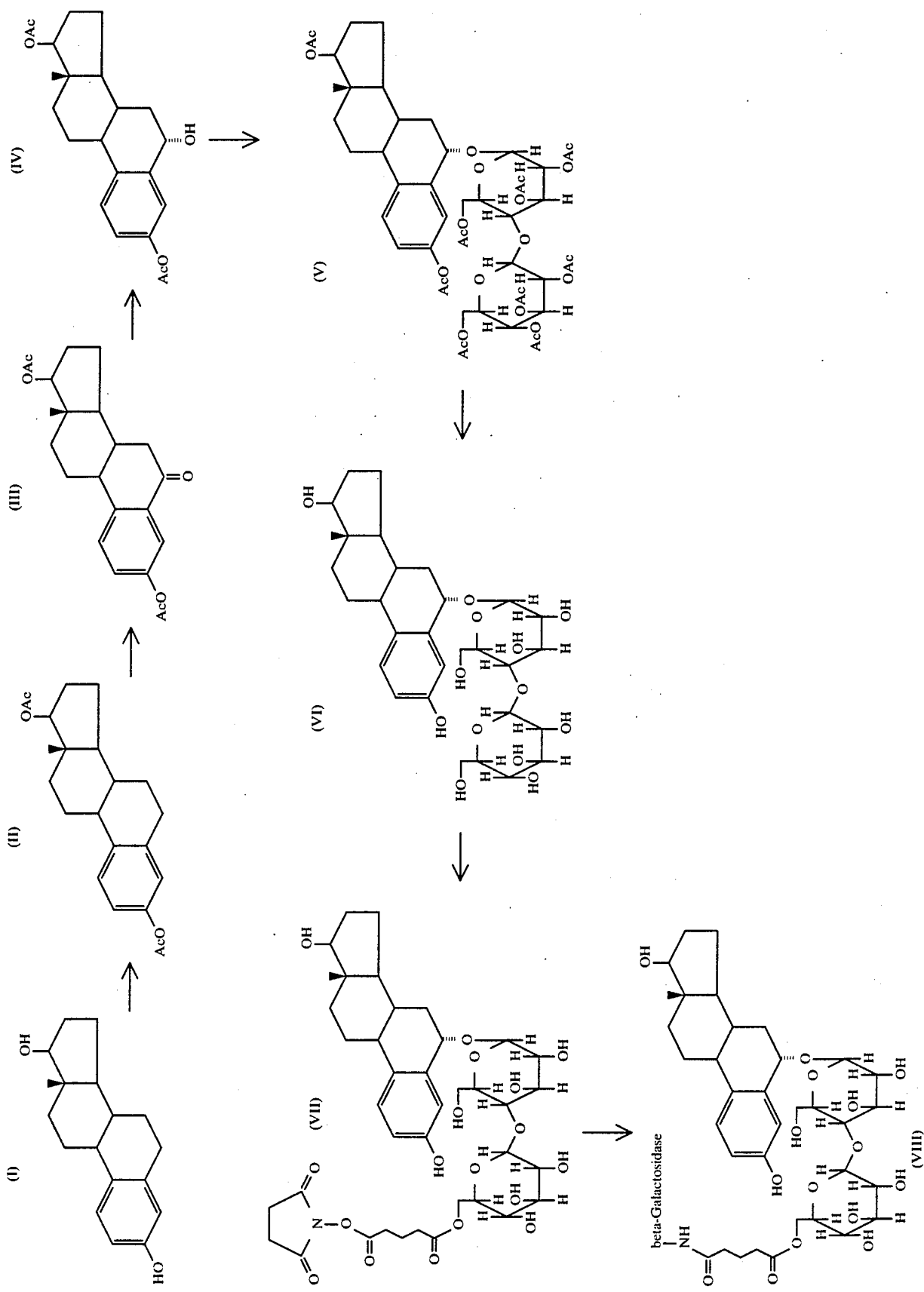

EXAMPLE 2 a) Diphenylhydantoin-4'-tetraacetylglucoside (II)

1.07 g. (8 mMole) 5-(4-Hydroxyphenyl)-5-phenylhydantoin (I), together with 2.36 g. (4.8 mMole) tetraacetylglucose trichloroacetimidate (preparation analogous to the procedure of R.R. Schmidt and J. Michel, Angew. Chem., 92, 763/1982), were dissolved in 40 ml. anhydrous tetrahydrofuran. 0.15 ml. Boron trifluoride etherate in 5 ml. anhydrous tetrahydrofuran was added dropwise thereto, while stirring. After stirring for 16 hours at ambient temperature, a further 0.98 g. (2 mMole) tetraacetylglucose trichloroacetimidate and 0.1 ml. boron trifluoride etherate were added thereto and stirring continued for a further 4 hours. Thereafter, the reaction mixture was mixed with 2 g. sodium hydrogen carbonate, filtered and the filtrate evaporated in a vacuum. The residue was extracted with 20 ml. acetone, the extract was evaporated in a vacuum and the product was separated by preparative column chromatography on silica gel (eluent: ethyl acetate/petroleum ether 2:1 v/v). Yield: 1.38 g. (52% of theory).

b) Diphenylhydantoin-4'-glucoside (III)

1.2 g. (2 mMole) of (II) were dissolved in 15 ml. methanol and mixed with 100 mg. sodium ethylate. The reaction mixture was stirred for 20 hours at 25° C., then 1 g. Amberlite LG 50 H+ was added thereto and stirring continued for a further 15 minutes. The reaction mixture was filtered and the filtrate evaporated in a vacuum. The crude product was dissolved in a little methanol, applied to a silica gel column and eluted with chloroform/methanol (3:1 v/v). Yield: 520 mg. (61% of theory).

c) Diphenylhydantoin-4'-glucose hemiglutaryl-N-hydroxysuccinimide ester (IV)

0.43 g. (1 mMole) of (III) was dissolved in 10 ml. anhydrous tetrahydrofuran and mixed with 0.87 g. (3 mMole) glutaric acid ω-0-trimethyl ester ω'-N-hydroxysuccinimide ester. 40 mg. P-Toluenesulphonic acid were added to the solution which was then stirred for 20 hours at 25° C. Subsequently, the solution was evaporated in a vacuum, the residue was dissolved in 30 ml. ethyl acetate and washed with 20 ml. each of 0.1N hydrochloric acid and water. The organic phase was dried with 5 g. anhydrous sodium sulphate and evaporated in a vacuum. The product (IV) was separated from the mixture by preparative column chromatography on silica gel (eluent: ethyl acetate/tetrahydrofuran 3:1 v/v). Yield: 0.26 g. (41% of theory).

d) Diphenylhydantoin-glucose immunogen (V)

50 mg. of activated hapten (V) were dissolved in 5 ml. dimethylformamide and added to a solution of 1 g. bovine serum albumin in 50 ml. 0.1N phosphate buffer (pH 8.5). The reaction mixture was stirred for 5 hours at 25° C., dialysed against water and lyophilized. The lyophilizate was washed with acetone, dried in a vacuum and used for immunisation.

The reaction scheme is illustrated in the following:

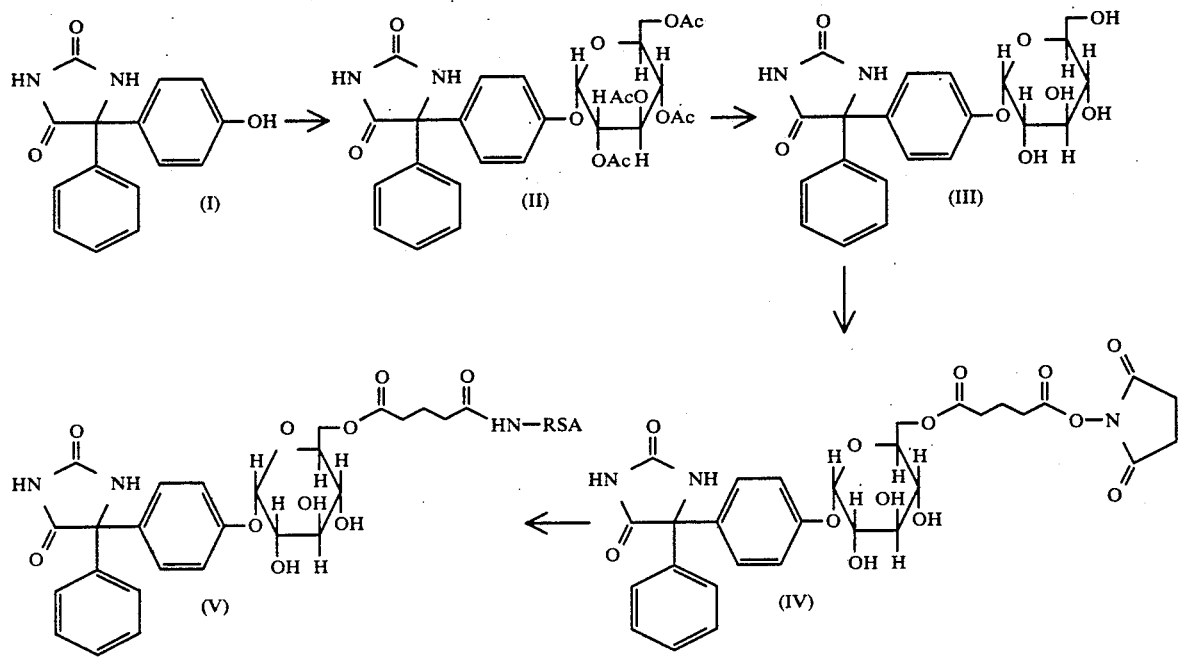

EXAMPLE 3

Antisera were produced by immunization with immunogens according to the present invention and immunogens of the prior art and their cross-reactivities were compared.

For this purpose, 10 sheep were first immunized with 100 μg. of immunogen in Freud's adjuvant and further immunized in an about 8 week rhythm with, in each case, 50 μg. of immunogen. After 60 or 150 days, the antiserum was removed and purified immunosorptively.

Estradiol-protein conjugates were used as immunogens. As carrier protein, in all cases β-galactosidase was used. For series 1-3, the binding to estradiol took place according to the prior art with carboxymethoxime (cmo), dimethylcarboxymethoxime (dmc) and hemisuccinate (hs) (see Steroid Biochem., 22, 285/1985; Chem. Pharm. Bull., 22, 1167/1974; Steroids, 23, 549/1974). The formulae for compounds 1 to 3 are shown in the following:

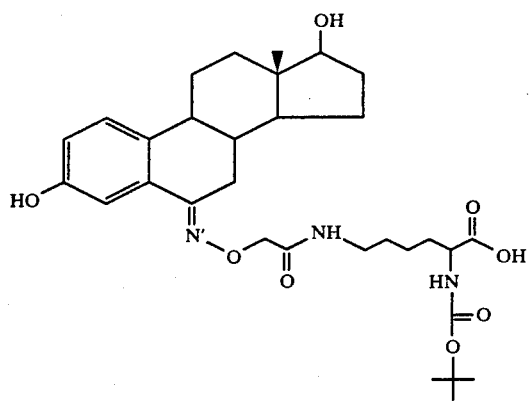

(1)

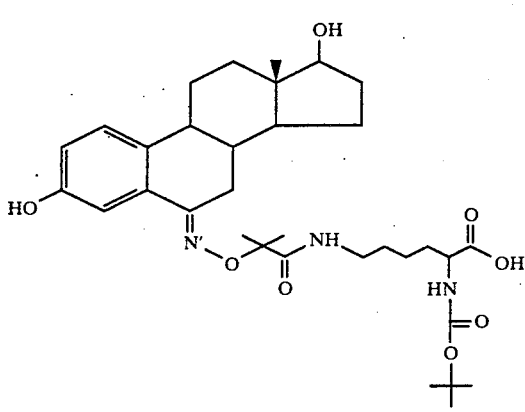

(2)

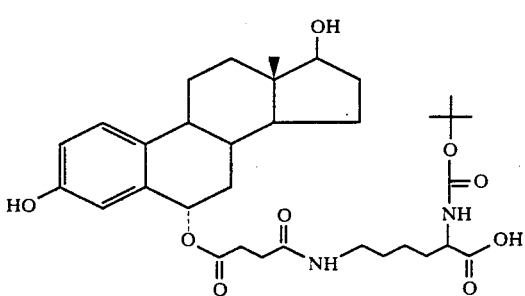

(3)

In the case of three further series (4–6), there was used an immunogen according to the present invention with glucose as bridge builder. The preparation took place analogously to Example 2.

Determination of the cross-reactivity

1. Reagents

Coating buffer:
50 mMole/litre sodium carbonate (pH 9.6).
Sample buffer:
10 mMole/litre sodium phosphate (pH 7.4); 0.9% sodium chloride; 0.1% Tween 20 and 1% crotein C.
Wash buffer:
0.9% sodium chloride and 0.1% Tween 20.
Antibody-enzyme conjugate:
25 mU/ml. of conjugate of peroxidase and a polyclonal antibody from rabbits, which is directed against sheep Fcγ, dissolved in sample buffer.
Substrate:
1.9 mMole/litre ABTS ® (2,3'-azino-di-(3-ethylbenz-thiazoline-6-sulphonic acid diammonium salt).
Polyhapten:

Eestradiol bound to rabbit IgG; preparation analogous to Example 1.7.

In series 1–3, there was used a polyhapten analogously to Example 1.7. In series 4–6, there was used a polyhapten which was produced analogously to Example 1.7 but in which estradiol-6-cmo-N-hydroxy-succinimide ester was used as activated hapten.

estradiol derivatives:
estradiol-6-cmo- ε-lysine (1)
estradiol-6-dmc- ε-lysine (2)
estradiol-6-hs- ε-lysine (3)
6-glucosyl-estradiol (preparation analogous to Example 1.5).

The preparation of cmo/dmc/hs- ε-lysine-modified estradiols took place by dissolving 1 mMole/litre estradiol-6-cmo/dmc/hs-N-hydroxysuccinimide ester and 1 mMole/litre N-α-tert.-butyloxycarbonyllysine in 5 ml. dimethylformamide and incubating for 2 days at ambient temperature. The product was precipitated out by the dropwise addition of diisopropyl ether and dried in a vacuum.

Antibody titration

In a preliminary experiment, the amounts of antibody to be used in the actual specificity experiments were determined. For this purpose, microtitre plates with 100 pg./cup of a solution of 1 pg. polyhapten/ml. of coating buffer were incubated at ambient temperature for 1 hour, while shaking. Subsequently, washing was carried out three times with wash buffer.

100 μof the antiserum (dilution series from 1:100 4th step in sample buffer) were added per cup and shaken for 1 hour at ambient temperature. Subsequently, washing was carried out three times with wash buffer.

100 μl. of antibody-enzyme conjugate were added thereto, shaken for 1 hour at ambient temperature and washed three times with wash buffer.

The detection reaction was initiated by the addition of 100 μl. of substrate/cup. After 15 minutes at ambient temperature, measurement was carried out at 405 nm (reference wavelength 490 nm).

The antiserum dilution associated with the half maximum binding was defined as titre. This amount of antibody was used in the following experiments.

Specificity of the antiserum (cross-reaction)

For the investigation of the specificity of the antiserum, the reactivities with the components available in solution were compared with one another.

The microtitre plates (A) with 100 μl./cup of a solution of 1 μg./polyhapten/ml. in coating buffer were incubated for 1 hour at ambient temperature and washed three times with wash buffer.

Antiserum (in double titre concentration) and antigen (dilution series from 5 μg. estradiol derivative/ml. of sample buffer, with sample buffer in the 4th step) were mixed in microtitre plate (B) pre-coated with 1% crotein C (50 μl. +50 μl.) and incubated for 30 minutes at ambient temperature. 100 μl. aliquots of the mixtures were transferred into the microtitre plates (A) coated with polyhapten. Incubation was carried out for 1 hour at ambient temperature with shaking, followed by washing three times with wash buffer.

100 μl. of antibody-enzyme conjugate/cup were added thereto and shaken for 1 hour at ambient temperature. Subsequently, washing was carried out three times with wash buffer.

The detection reaction was initiated by the addition of 100 μl. of substrate/cup and measured at 405 nm (reference wavelength 490 nm) after 15 minutes at ambient temperature.

The concentration of the antigen associated with the half maximum binding is defined as relative affinity.

For the comparison of the reactivity of an antiserum with various estradiol derivatives, the relative affinity of estradiol is taken as being 100%. The reactivities (corresponding to the cross-reactions) are given from the percentages of the relative affinity:

$$\text{cross-reaction} = \frac{c\text{rel. aff. }\phi\text{estradiol (nM)}}{c\text{rel. aff. X (nM)}} \times 100\%$$

The results obtained are given in the following Table I. The superiority of the immunogens with sugar bridges is hereby clearly shown by the substantially lower cross-reaction in comparison with the homologous estradiol derivative which, in turn, is a quantitative expression for the antibody directed against the linker itself. The lower is the cross-reaction, the better is the result.

TABLE I

| series | homologous φestradiol derivative | cross-reaction with the homologous derivative (%) sample 1 | sample 2 |
| --- | --- | --- | --- |
| 1 | φestradiol-6-cmo-ε-lysine | 1040 | 770 |
| 2 | φestradiol-6-dmc-ε-lysine | 770 | 180 |
| 3 | φestradiol-6-hs-ε-lysine | 1950 | 620 |
| 4 | 6-glucosyl-φestradiol | 191 | 119 |
| 5 | 6-glucosyl-φestradiol | 163 | 121 |
| 6 | 6-glucosyl-φestradiol | 373 | 244 | sample 1: serum sampling 60 days after first immunization
sample 2: serum sampling 150 days after first immunization

We claim:

1. Hapten-sugar-protein conjugate, comprising a hapten, a sugar of from 1 to 10 monosaccharide units which may be the same or different and having a free $CH_2OH$ group and a hydroxyl group on one end and a reducing end at the opposite end wherein said free $—CH_2OH$ group is in the $\alpha$ position to the hydroxyl group, and a protein, wherein said protein is bound directly or via a bridge molecule to said free $CH_2OH$ group and said hapten is bound to said reducing end.

2. Hapten-sugar-protein conjugate of claim 1, wherein said sugar comprises pyranoses or furanoses.

3. Hapten-sugar-protein conjugate of claim 1 wherein said sugar is lactose, cellobiose, maltose or maltopentaose.

4. Hapten-sugar-protein conjugate of claim 1, wherein said hapten is a steroid hormone with a hydroxyl group on its $C_6$ atom via which said hapten is bound to said sugar.

5. Hapten-sugar-protein conjugate of claim 4, wherein said steroid hormone is estradiol.

6. Hapten-sugar-protein conjugate of claim 1, wherein said protein is an enzyme.

7. Hapten-sugar-protein conjugate of claim 6, wherein the enzyme is $\beta$-galactoisidase or peroxidase.

8. Hapten-sugar-protein conjugate of claim 1, wherein said protein is an immunogenic protein.

9. Hapten-sugar-protein conjugate of claim 1, wherein said protein is bound directly to said free $CH_2OH$ group.

10. Hapten-sugar-protein conjugate of claim 1, wherein said protein is bound via a bridge molecule to said free $CH_2OH$ group.

11. Hapten-sugar-protein conjugate of claim 1, wherein said sugar contains from 1 to 5 monosaccharide units.

12. Hapten-sugar-protein conjugate of claim 10, wherein said protein is beta galactosidase, said bridge molecule is an N-hydroxysuccinimide ester, said sugar is maltose and said hapten is estradiol.

* * * * *

UNITED STATES PATENT AND TRADEMARK OFFICE
CERTIFICATE OF CORRECTION

PATENT NO. : 5,032,518
DATED : July 16, 1991
INVENTOR(S) : Erasmus Huber et al.

It is certified that error appears in the above-identified patent and that said Letters Patent is hereby corrected as shown below:

Column 1, line 47: change "Dalton" to -- Daltons --.

Column 2, line 22: change "$CH_2OG$" to -- $CH_2OH$ --.

Column 2, line 46: change "a-position" to -- $\alpha$-position --.

Column 5, line 3: change "6$\epsilon$ " to -- 6$\alpha$ --.

Column 6, line 4: change "6$\epsilon$ " to -- 6$\alpha$ --.

Column 9, line 68: change "P-Toluene" to --p-Toluene--

Column 12, line 27: change "100 pg/cup" to --100 µg./cup--.

Column 12, line 27: change "1 pg poly" to --1 µg. poly--.

Column 12, line 32: change "100u of" to --100 µl. of--.

Signed and Sealed this

Twenty-seventh Day of April, 1993

*Attest:*

MICHAEL K. KIRK

*Attesting Officer*   *Acting Commissioner of Patents and Trademarks*